United States Patent [19]

Rosevear et al.

[11] Patent Number: 4,753,985

[45] Date of Patent: Jun. 28, 1988

[54] SYNTHESIS OF ORGANIC COMPOUNDS USING DEFORMABLE GEL IN POROUS RIGID SUPPORT

[75] Inventors: Alan Rosevear, Wantage; Robert C. Sheppard, Cambridge, both of England

[73] Assignee: United Kingdom Atomic Energy Authority, London, England

[21] Appl. No.: 873,309

[22] Filed: Jun. 9, 1986

Related U.S. Application Data

[63] Continuation of Ser. No. 406,057, Aug. 6, 1982, abandoned.

[30] Foreign Application Priority Data

Oct. 7, 1981 [GB] United Kingdom ............... 8130342

[51] Int. Cl.[4] ................... C08F 283/00; A61K 37/02
[52] U.S. Cl. ................... 525/54.11; 530/334
[58] Field of Search ............... 525/54.1, 54.11; 521/55; 428/402; 435/172; 536/22; 523/218; 427/212, 213.34, 215, 221; 530/333, 334

[56] References Cited

U.S. PATENT DOCUMENTS

| | | |
|---|---|---|
| 3,943,072 | 3/1976 | Thomson et al. |
| 4,192,798 | 3/1980 | Verlander et al. ............... 525/54.11 |
| 4,335,017 | 6/1982 | Miles et al. ............... 435/178 |
| 4,673,734 | 6/1987 | Tayot et al. ............... 530/364 |

OTHER PUBLICATIONS

Atherton et al., *J. Am. Chem. Soc.*, 97: 22, 6584–5 (1975).
Schmitt et al., *FEBS Letters*, 81: 2, 403–405 (1977).
Merrifield, *J. Am. Chem. Soc.*, 85, 2149–2154 (1963).
Arshady et al., *J. Chem. Soc. Perkin I*, 529–537 (1981).
Brown et al., *J. Chem. Soc. Perkins I*, 1161–1167 (1983).
Brown et al., *J. Chem. Soc. Chem. Comm.*, 1093–1095 (1980).
Brown et al., *J. Chem. Soc. Perkin I*, 75–82 (1983).
Atherton et al., "Synthesis of a 21-Residue Fragment of Human Proinsulin by the Polyamide Solid Phase Method", *Hoppe-Seyler's Z. Physiol. Chem.*, Bd. 362, S. 833–839, Jul. 1981.

*Primary Examiner*—Delbert R. Phillips
*Assistant Examiner*—Nathan M. Nutter
*Attorney, Agent, or Firm*—Larson and Taylor

[57] ABSTRACT

The present invention relates to the synthesis of chemical compounds and more particularly to the synthesis of organic compounds, for example, peptides and oligonucleotides.

The invention provides a composite material for use in the synthesis of organic compounds comprising a support material and, supported on the support material, an organic compound synthesizing substance.

It is preferred that the organic compound synthesizing substance is a gel (e.g. a dimethylacrylamide copolymer gel).

The invention also provides a method for preparing a composite material for use in the synthesis of organic compounds and a method for the synthesis of organic compounds.

8 Claims, No Drawings

SYNTHESIS OF ORGANIC COMPOUNDS USING DEFORMABLE GEL IN POROUS RIGID SUPPORT

This application is a continuation, of application Ser. No. 406,057 filed Aug. 6, 1982, now abandoned.

The present invention relates to the synthesis of chemical compounds and more particularly to the synthesis of organic compounds, for example, peptides and oligonucleotides.

According to one aspect of the present invention there is provided a composite material, for use in the synthesis of an organic compound, comprising a support material and, supported on the support material, an organic compound synthesising substance.

It will be appreciated that "organic compound synthesising substance" as used in this specification means a substance capable of participating in the synthesis of an organic compound. It is preferred that the organic compound synthesising substance is an organic compound synthesising gel (i.e. a gel capable of participating in the synthesis of an organic compound). Such gel may contain activated substituents upon which an organic polymeric compound can be synthesised by sequential additions of units (e.g. amino acid or nucleotide units).

Examples of known organic compound synthesising gels are substituted polydimethylacrylamide gels, which may be used in the synthesis of peptides and in the synthesis of oligonucleotides.

Conventionally a discontinuous mode of operation is adopted when using gels for peptide synthesis. Thus the gel is treated sequentially with acylating and deprotecting agents in a shaken or stirred reaction vessel. Excess reagents are removed by filtration and repeated washing steps. It has been recognised that substantial advantages may accrue if a flow type mode of operation could be adopted. Thus, introduction and removal of reagents and washing media could be more rapid and process control could be simplified offering the possibility of automated control.

However, known organic compound synthesising gels tend to be deformable (i.e. non-rigid) and have physical properties which make them difficult or unsuitable to apply in flow through operation. Thus, for example, a known polyamide gel suitable for use in the synthesis of peptides (E. Atherton et al, J. Amer. Chem. Soc., 1975, 97, 6585; R. Arshady et al, J. Chem. Soc. Perkin I, 1981, 529) was found to pack down under the influence of pumped flow conditions with the destruction of its open matrix character and the generation of high pressures.

Similar high pressure difficulties have been encountered with polystyrene gels.

The present invention may be employed substantially to avoid or reduce the abovementioned difficulties, since the deformable (i.e. non-rigid) gel is supported by the support material and the composite is thus able to resist deformation under flow conditions.

Preferably the support material is a porous rigid support material and the organic compound synthesising substance is retained within the pore structure of the porous rigid support material.

It is preferred, in accordance with the present invention, that the porous rigid support material is in the form of discrete porous particles having an interconnected pore structure (for example those particles of inorganic material which may be prepared by a method as claimed in any one of claims 1 to 9 or claim 15 of British Pat. No. 1,421,531 (UKAEA). (U.S. Pat. No. is 3,943,072 corresponds to BP 1421531). For example, discrete porous particles of inorganic oxides (such as titania) or of a natural earth (such as Celite (Registered Trade Mark) or Keiselguhr) prepared in accordance with BP 1421531 may be used as a porous rigid support material in accordance with the present invention.

In accordance with one preferred embodiment of the present invention there is provided a composite material, for use in the synthesis of an organic compound, comprising discrete particles of porous rigid support material and, retained within the pore structure of the porous rigid support material, an organic compound synthesising gel.

Where the substance is retained in the pore structure of the porous rigid support material it will be appreciated that the porous rigid support material provides a rigid "skeleton" having dimensional stability as a support for the substance. Thus, in accordance with the present invention, organic compound synthesising substances which are difficult or inconvenient to handle because of their physical nature (e.g. gels which will undergo dimensional changes when subject to pressures normally encountered in column operations (e.g up to $\sim$3 atmospheres) and deform to cause an increase in back pressure), are part of a composite material which, due to the rigidity imparted by the porous rigid support material "skeleton", can be handled and used more easily.

Where the composite material comprises, for example, discrete porous particles with a gel retained therein the composite material can be loaded into, and used, conveniently in column systems.

In accordance with the present invention particles of composite material can be formed which tend to settle readily in aqueous or organic media and can be used to form columns having good flow properties. Also the particles of composite material tend to be stable and not liable to release "fines".

Particles of composite material can be introduced into columns and used to synthesise organic compounds such as peptides and polynucleotides in a flow type operation.

British Patent Specification No. 1,421,531 discloses and claims, inter alia:

"A method for producing discrete porous particles for the selective retention of macromolecules from a fluid substance containing said macromolecules, said discrete porous particles having interconnected porosity throughout, which method includes the steps of preparing discrete green particles from a mixture containing solid particles of a finely divided, substantially insoluble, sorptive (as defined in the Specification), inorganic material and a fugitive additive in solution, said mixture being formed by mixing said solid particles of inorganic material with a fugitive additive and a solvent therefor, said fugitive additive being for subsequently providing a pore structure in the inorganic material and said inorganic material being substantially insoluble in the solvent for the fugitive additive, the preparation of the discrete green particles being such that, and the fugitive additive being selected such that, the fugitive additive is provided in solid form in the green particles, and heating the green particles to remove fugitive additive therefrom and cause sintering of inorganic material to give discrete porous particles, the fugitive additive and the amount thereof in the green particles being selected such that the discrete porous particles have an interconnected porosity throughout the discrete porous particles providing an extended surface area and the pore structure is such as will allow the macromolecules to permeate the discrete porous particles and be sorbed."

British Pat. No. 1,421,531 also claims discrete porous particles made by the method claimed therein.

Discrete porous particles for use in accordance with the present invention preferably have a porosity of >20% and an interconnected porosity with pores ≧2000 Å such as to allow both the organic compound synthesising substance to occupy the pores and the release of synthesised organic compound.

Other materials having dimensional stability, such as porous glass, foam metal and macroreticular porous organic polymers, may be used as support materials in accordance with the present invention.

Where the organic compound forming substance is retained within the pore structure of a porous rigid support material it is preferred that the majority of the substance (e.g. a gel) is present in the internal pore structure of the porous rigid support material. However, it will be appreciated that some gel may also be formed on the surface of the support material.

According to another aspect of the present invention there is provided a method for preparing a composite material for use in the synthesis of organic compounds, said composite material comprising a support material and, supported on the support material, an organic compound synthesising substance, said method comprising introducing a precursor for the substance to the support material and treating the precursor to form the substance on the support material.

In one embodiment of the immediately preceeding aspect of the invention there is provided a method for preparing a composite material for use in the synthesis of organic compounds comprises introducing a precursor for an organic compound synthesising substance into the pore structure of a porous rigid support material and treating the precursor to form the substance in the pore structure.

The precursor may be in a solution (e.g. in mixed water/ DMF).

Where it is desired to produce a composite in which the majority of the organic compound synthesising substance is retained in the pore structure of a porous support material the preparation of the composite can be controlled to assist in maximising the amount of the deformable substance retained in the pore structure of the porous rigid support material. Thus, for example, where in accordance with an embodiment of the method of the invention a solution of precursor is contacted with a porous rigid support material to introduce precursor into the pore structure, the volume of the solution of precursor contacted with the support material (e.g. by soaking the support material in the solution) can be chosen such that it is approximately equal to the volume required to fill the pore structure (i.e. to minimise the amount of substance formed outside the pore structure the volume of the solution should not substantially exceed the volume required to fill the pore structure).

Also the volume of any reagent solutions used to treat the precursor in the pore structure to form the substance can be chosen such that it is not substantially in excess of that required to immerse the porous rigid support material.

Additionally, if required, loosely adhering substance (e.g. non-rigid gel) may be removed from particles of composite material after formation of the substance by washing and, if necessary, mechanical means, (e.g. sieving) prior to use.

Thus, in accordance with the present invention a composite material can be produced in which there is the minimum of deformable substance outside of the internal pore struqture of a porous rigid support material. For example, the porous rigid support material may be in the form of discrete porous particles and a minimum of deformable substance may be formed between the particles so that substantially all of the substance formed is retained by the particles with the majority of the deformable gel being in the internal pore structure thereof, thereby to give a composite material in the form of discrete particles. With this particulate form of composite material, inter alia, handling and column packing may be aided in addition to column operation.

An organic compound synthesising gel may be formed in accordance with the present invention, for example, by a method which includes polymerisation and cross-linking to form a gel comprising a gel network.

Thus, in one embodiment a solution of a polymerisable precursor in water or mixed water/organic solvent can be introduced into the pores of a porous rigid support material and then treated to effect polymerisation and cross-linking to form a gel comprising a gel network. The polymerisation and cross-linking may be effected, for example, by including in the solution an agent which will generate free radicals (e.g. persulphate) or, for example, by use of external agents such as nuclear radiation or heat. The gel can be functionalised (e.g. with carboxymethyl groups) during polymerisation by inclusion of a functionalising agent in the solution.

Alternatively the gel can be functionalised (e.g. with subsequently to polymerising carboxymethyl groups) prior to use in the synthesis of chemical compounds (e.g. peptides and nucleotides). By way of example a polymethylacrylamide gel can be formed in the pores of particles of Kieselguhr fabricated in accordance with BP 142531 by introducing a precursor for the gel into the particles, polymerising the precursor to form a gel and functionalising the gel.

According to a further aspect the present invention provides a process for the synthesis of an organic compound which comprises treating a composite material comprising a support material and, supported on the support material, an organic compound synthesising substance, to produce the compound on the substance, and recovering the compound from the substance.

In accordance with one embodiment of the immediately preceding aspect of the present invention there is provided a process for the synthesis of a peptide which comprises treating a composite material comprising a porous rigid support material and, retained in the pore structure of the porous rigid support material, an organic compound synthesising gel, with reagents to bond an amino acid or peptide unit to the gel and to cause repeated coupling of amino acid or peptide units to the bonded amino acid or peptide unit thereby to build up a peptide chain.

In accordance with another embodiment of the immediately foregoing aspect of the present invention there is provided a process for the synthesis of an oligonucleotide which comprises treating a composite material comprising a porous rigid support material, and retained in the pore structure of the porous rigid support material, an organic compound synthesising gel, with reagents to bond a nucleotide unit to the gel and to cause repeated coupling of nucleotide units to the bonded nucleotide unit thereby to build up an oligonucleotide chain.

By way of example only, reference may be made to the R. Arshady et al publication hereinbefore mentioned in relation to the building up of peptide chains.

Examples of peptides that have been synthesised in accordance with the present invention are the Merrifield-Dorman test tetrapeptide Leu. Ala. Gly. Val, its isomer Leu. Ala. Val. Gly, an undecapeptide amide from the HLA-DR antigen sequence (P. Altevogt et al, Eur. J. Immunol, 1980, 10, 908) and several peptides from the gastrin series.

It will be appreciated that the organic compound synthesising substance and the support material should be substantially insoluble in fluid substances with which they may be contacted in use (e.g. acylating and deprotecting agents).

The present invention also provides a composite material for use in the synthesis of an organic compound whenever prepared by a method in accordance with the present invention.

Further the present invention also provides a composite material, for use in the synthesis of an organic compound, obtainable by a method in accordance with the present invention.

Also the present invention provides an organic compound whenever synthesised by a process in accordance with the present invention.

The present invention may also be employed in protein sequencing.

The invention will now be further described by reference to the following Examples:

EXAMPLE 1

In this Example a composite material was prepared by polymerising a solution of acrylate monomers under anaerobic conditions in discrete porous particles of Kieselguhr fabricated in accordance with BP 1421531.

Thus (under nitrogen) an aqueous solution of ammonium persulphate (10% w/v, 7.5 ml) was added to a solution of freshly distilled dimethylacrylamide (10g), ethylene-bisacrylamide (1.17 g) and freshly distilled acryloyl sarcosine methyl ester (0.85 g) in dimethylformamide (16 ml) and water (25 ml). The resulting mixture was soaked into fabricated porous Kieselguhr particles (29 g; 355–500 $\mu$dia. prepared in accordance with BP 1421551), and polymerisation allowed to proceed for 2 $\frac{1}{2}$h at room temperature. The resulting composite material particles were washed with water and any agglomerated particles separated and unbound polymer gel removed. The particles were then washed in acetone/water (1:2), acetone, diethyl ether and dried in vacuo. The composite material particles (30.9 g) were treated to functionlise the gel therein with carboxymethyl groups to the extent of 0.046 meq/g (sarcosine content).

[The procedure of Example 1 has been used with appropriate choice of conditions, to produce composite materials with a sarcosine content of up to 0.237 meq/g.]

[Also the procedure of Example 1 has been used to produce composite materials which generate negligible back pressure in column use at flow rates (dimethylformamide) of 100 ml/h/cm$^2$].

EXAMPLE 2

Particles of composite material were prepared as follows:

Freshly distilled dimethylacrylamide (10 g), acryloyl sarcosine methyl ester (0.86 g) and NN'-ethylene-bisacrylamide acrylamide (1.16 g) were dissolved in dimethylformamide (16 ml) and water (25 ml). Nitrogen gas was bubbled through the mixture for 15 min. A 10% w/v aqueous solution of ammonium persulphate (7.5 ml) was added and the resulting mixture poured onto fabricated Keiselguhr particles (75 ml packed volume, 355–500 $\mu$dia, 0.39 g/cc, prepared in accordance with BP 1421531). This resulting stiff paste was placed in a vacuum dessicator for 20 minutes after which the vacuum was broken under nitrogen. After a further 2 hr 10 mins the resulting product was washed with distilled water (5×300 ml) forced through a 710$\mu$ sieve to break up any aggregates and then washed in 1:2 acetone/water (2×150 ml), acetone (5 ×150 ml) and finally diethyl ether (2×100 ml). The product was air dried to give free flowing particles of composite material with a packing density of 0.41 g/cc and sarcosine content of 0.046 mmoles per gram of particles.

EXAMPLE 3

Particles of composite material were prepared as follows:

Freshly distilled dimethylacrylamide (9 g), acryloyl sarcosine methyl ester (1.7 g) and NN'-ethylene-bisacrylamide (1.16 g) were dissolved in dimethylformamide (16 ml) and water (25 ml). Nitrogen gas was bubbled through the mixture for 15 min. A 10% w/v aqueous solution of ammonium persulphate (7.5 ml) was added and the resulting mixture poured onto fabricated porous Keiselguhr particles (30 g, 355–500 $\mu$ dia prepared in accordance with BP 1421531). The mixture thereby produced was placed in a vacuum dessicator for 50 min. after which the vacuum was broken under nitrogen. After a further 1hr 40 min the resulting product was washed as in Example 2. The sarcosine ester content of those resulting particles of composite material was found to be 0.156 mmoles/g.

EXAMPLE 4

Particles of composite material were prepared as follows:

A monomer mixture containing persulphate was prepared as in Example 3 and poured onto fabricated porous keiselguhr particles (30 g, 210–300 $\mu$ dia. prepared in accordance with BP 1421531). The resulting mixture was kept in a vacuum dessicator for 20 min and then left under nitrogen for 24 hrs before washing as in Example 4. The resulting particles of composite material were found to have a sarcosine content of 0.237 mmoles/g.

EXAMPLE 5

Particles of a composite material containing a polystyrene gel were prepared as follows:

Damp benzoyl peroxide (0.4 g) was dissolved in styrene (15 ml) containing divinylbenzene (0.3 ml as 1:1 DVB: vinyl ethyl benzene). 12 ml of the resulting mixture were added to fabricated porous Kieselguhr beads (355–500 $\mu$ dia., 10.47 g 20 ml, prepared in accordance with BP 1421531). The particles containing the styrene were placed on a water bath at 70° under an atmosphere of nitrogen for 2 hrs. The particles were then heated at 70° for a further 11 hrs. The resulting particles of composite material were washed free of unbound polystyrene with methylene chloride (10×100 ml) and any agglomerates broken up by forcing through a 700μ sieve. The organic content (polystyrene) of the resulting particles of composite material was found to be 14.3% by weight.

EXAMPLE 6

In this Example a particulate composite material fabricated in accordance with the procedure of Example 1 was used in the synthesis of the gastrin-related octapeptide amide Glu. Ala. Tyr. Gly. Trp. Leu. Asp. Phe. NH$_2$ (hereinafter referred to as (I)).

Thus, a composite material comprising particles of Keiselguhr and polydimethylacrylamide gel were produced in accordance with the procedure of Example 1 (3.45 g, 8 ml) and were functionalised by reaction with ethylene diamine (15 ml) for 16 h. The particles were then filtered and washed well with dimethylformamide (DMF), and a portion (6.5 ml, ca. 0.12 meq) of the resulting slurry of particles was packed in a 15 mm diam. glass column. The column was connected to a simple PTFE valving and pumping system permitting reagent selection, flow, and recirculation. Effluent from the column was monitored continuously at 308 m μ. Freshly prepared fluorenyl-methoxycarbonyl-norleucine anhydride (internal reference amino-acid) (see E. Atherton et al, J. Chem. Soc. Perkin I, 1981, 538) (0.5 m mole) in DMF (0.5 ml) was added to the top of the column and recirculated at a flow rate of 3.3 ml/m for 1 h. (A sample of particles withdrawn after 30 min gave a negative ninhydrin test). The column was washed with DMF (15 min), Fmoc groups cleaved with 20% piperidine-DMF (10 min), and the particles washed again with DMF (30 min). Further acylation steps were then carried out with 0.5 m moles of the trichlorophenyl ester of p-hydroxymethylbenzoic acid (peptide resin linkage agent) in the presence of hydroxybenzotriazole, and then Fmoc-phenylalanine anhydride in the presence of N-methylmorpholine (1 equiv) and p-dimethylaminopyridine (0.1 equiv) (esterification of the first amino-acid residue to the gel) (see E. Atherton et al, J. Chem. Soc. Chem. Comm. 1981, 936). The remaining seven residues of the octapeptide sequence (I) were added successively using Fmoc-amino-acid anhydrides with t-butyl side chain protection as appropriate. After addition of the glycine residue, subsequent steps were program controlled with acylation time 51.2 min (ninhydrin test at 25.6 min), DMF wash 12.8 min, deprotection 9.6 min, DMF wash 25.6 min, total cycle time 99.2 min. Wash times were set arbitrarily. All ninhydrin reactions were negative at the first test.

Samples for amino-acid analysis were removed after step 4 (Found: Leu, 0.98; Asp, 1.02; Phe, 1.00; Nle, 1.06), and step 8 (Found: Glu, 1.02, Ala, 0.95; Tyr, 1.01; Gly, 1.03; Leu, 0.97; Asp, 1.00; Phe, 1.00; Nle 1.08). Side chain protecting groups were removed from the octapeptide (I), which was bound to the gel of the composite, by treatment with 90% trifluoroacetic acid (30 min), and the octapeptide amide (I) detached with saturated methanolic ammonia (18 h). The total product (Found: Glu, 1.07; Ala, 1.02; Tyr, 1.01; Gly, 1.04; Leu, 0.98; Asp, 1.04; Phe, 1.00) was chromatographed on diethylaminoethyl cellulose. The octapeptide amide (I) recovered from the main peak (Found: Glu, 1.07; Ala, 1.02; Tyr, 1.00; Gly, 1.03; Leu, 0.99; Asp, 1.01; Phe, 1.00) was found to be identical by HPLC and TLC studies to the product obtainable using unsupported peptide synthesising gels. The overall yield was 47%.

We claim:

1. In a process for the synthesis of an organic compound in which an organic compound is synthesized with a reagent on an organic compound synthesizing gel and in which the synthesized organic compound is subsequently recovered from the synthesizing gel, said synthesizing gel being deformable and subject to packing down under the influence of flow conditions, the improvement wherein said organic compound synthesizing gel is provided in the form of a composite particulate material capable of resisting deformation under said flow conditions, said particulate composite material comprising discrete porous rigid support particles having said organic compound synthesizing gel retained in the pore structure of the porous rigid support particles, said particles having an interconnected pore structure, the pore size of said particles being sufficiently large to permit said synthesizing gel to occupy the pores and to permit the release of the synthesized organic compound.

2. A process according to claim 1 wherein said organic compound comprises a peptide, said reagent being capable of bonding an amino acid or peptide unit to said organic compound synthesizing substance and being capable of causing repeated coupling of amino acid or peptide units to the bonded amino acid or peptide unit thereby to build up a peptide chain.

3. A process according to claim 1 wherein said organic compound comprises an oligonucleotide, said reagent being capable of bonding a nucleotide unit to the gel and being capable of causing repeated coupling of nucleotide units to the bonded nucleotide unit thereby to build up an oligonucleotide chain.

4. A process according to claim 1 wherein said organic compound synthesizing substance comprises a polyamide gel.

5. A process according to claim 1 wherein said organic compound synthesizing substance comprises a polymethylacrylamide gel.

6. A process according to claim 1 wherein said gel comprises a substituted polydimethylacrylamide gel.

7. A process ascccording to claim 1 wherein said porous rigid support particles comprise a member selected from the group consisting of inorganic oxides, a natural earth, porous glass, foam metal, and macroreticular organic polymers.

8. A process according to claim 7 wherein said porous rigid support particles have a porosity of greater than 20% and a pore size of at least 2000 Å.

* * * * *